(12) United States Patent
Lee et al.

(10) Patent No.: US 12,053,226 B2
(45) Date of Patent: Aug. 6, 2024

(54) SURGICAL NAVIGATION INSTRUMENT HAVING TEMPERATURE SENSOR

(71) Applicant: CHUNGWOO MEDICAL CO., LTD., Seoul (KR)

(72) Inventors: Il-Kwon Lee, Anyang-si (KR); Kee-Seok Lee, Seoul (KR); Jong-Jun Yim, Gwangmyeong-si (KR)

(*) Notice: Subject to any disclaimer, the term of this patent is extended or adjusted under 35 U.S.C. 154(b) by 381 days.

(21) Appl. No.: 17/546,259

(22) Filed: Dec. 9, 2021

(65) Prior Publication Data
US 2023/0157743 A1    May 25, 2023

(30) Foreign Application Priority Data
Nov. 24, 2021  (KR) .................... 10-2021-0163570

(51) Int. Cl.
*A61B 18/14* (2006.01)
*A61B 18/00* (2006.01)

(52) U.S. Cl.
CPC ...... *A61B 18/14* (2013.01); *A61B 2018/0013* (2013.01); *A61B 2018/00791* (2013.01); *A61B 2018/0091* (2013.01); *A61B 2018/0097* (2013.01)

(58) Field of Classification Search
CPC ............... A61B 18/14; A61B 18/1482; A61B 2018/0013; A61B 2018/00791; A61B 2018/0091; A61B 2018/0097; A61B 2090/0813; A61B 2218/007

USPC ...................................................... 606/41–50
See application file for complete search history.

(56) References Cited

U.S. PATENT DOCUMENTS

| | | | | |
|---|---|---|---|---|
| 4,931,047 A | * | 6/1990 | Broadwin | A61B 18/14 606/49 |
| 2006/0052774 A1 | * | 3/2006 | Garrison | A61B 17/22012 606/49 |
| 2011/0033823 A1 | | 2/2011 | Gersh et al. | |
| 2014/0155890 A1 | * | 6/2014 | Bernard | A61B 18/18 606/42 |

FOREIGN PATENT DOCUMENTS

| | | |
|---|---|---|
| KR | 10-0758026 B1 | 9/2007 |
| KR | 10-1027819 B1 | 4/2011 |
| KR | 10-1039111 B1 | 6/2011 |
| KR | 10-1490041 B1 | 2/2015 |

* cited by examiner

*Primary Examiner* — Michael F Peffley
(74) *Attorney, Agent, or Firm* — KORUS Patent, LLC; Seong Il Jeong

(57) ABSTRACT

Disclosed herein is a surgical navigation instrument having a temperature sensor. The surgical navigation instrument can easily perform an autoclave action to remove microorganisms using saturated steam with respect to a part which can be contaminated during treatment, and enhance convenience in replacement of a grip part and the electrodes of the handpiece which are consumables, since a handpiece and electrodes are detachably screw-coupled with each other.

13 Claims, 5 Drawing Sheets

SURGICAL NAVIGATION INSTRUMENT HAVING TEMPERATURE SENSOR

BACKGROUND OF THE INVENTION

Field of the Invention

The present invention relates to a surgical navigation instrument and, more specifically, to a surgical navigation instrument equipped with a temperature sensor, which can easily perform an autoclave action to remove microorganisms using saturated steam with respect to a part which can be contaminated during treatment.

Background Art

In general, a high frequency instrument, an ultrasonic surgical device or a liposuction surgical device used for surgical operations, such as laparoscopic surgery, thoracoscopic surgery, or hemorrhoidectomy, urologic surgery, such as prostatic surgery or bump removal, gynecological surgery, such as hysterotomy, head and neck surgeries, or obesity surgery includes: a control unit like a surgical device disclosed in Korean Patent No. 10-1039111, a hand switch or a foot switch, a handpiece for high frequency or ultrasonic surgery as a surgical navigation instrument connected to the control unit; and electrodes (cannula) joined to the handpiece and inserted into the human body. When a user operates the hand switch or steps the foot switch, the surgical device starts high frequency output or ultrasonic vibration to cut biological tissues and to absorb fat.

That is, the conventional high frequency surgical device or the conventional ultrasonic surgical device used as a surgical instrument is a surgical device for biological tissue incision or coagulation, and fat absorption using high frequency or ultrasonic waves, thereby enabling prompt surgery, bloodless incision, and minimization of damages of tissues, remarkably reducing an infection rate since foreign matters for vascular nodules are not remained, and promoting recovery of a surgical site. The conventional device converts electrical energy into high frequency output or ultrasonic vibration by a converter of the handpiece, transmit the high frequency output or the ultrasonic vibration to the electrodes inserted into the biological tissues so as to cause biological tissue incision or coagulation, and fat absorption at the same time.

However, in numerous instances, electrodes which do not have temperature sensors are mounted in the handpiece of the surgical device, and so, when high frequencies are output to the biological tissues, the electrodes which are in direct contact with the biological tissues cannot sense temperature but the handpiece which is away from the biological tissues senses temperature. Accordingly, the conventional surgical devices cannot precisely control phase and strength of the high frequency output applied to the biological tissues according to the change in the physical properties of the tissues, for instance, artery, the vein, the gastrointestinal tract, the intestinal membrane, the liver, the kidney, the stomach, the spleen, the prostate, etc., so that the tissues around the surgical site are damaged. Additionally, the conventional surgical devices have to perform repeated control work in order to adjust the optimum high frequency output according to the properties of the biological tissues, and so, the treatment time is lengthened.

However, the conventional surgical navigation instruments have several disadvantages in that it is difficult to replace a grip part and the electrodes of the handpiece which are consumables, and in that cleaning or an autoclave action is not performed properly at parts that can be contaminated.

PATENT LITERATURE

Patent Documents

Patent Document 1: Korean Patent No. 10-1039111 (published on Jun. 7, 2011)

SUMMARY OF THE INVENTION

Accordingly, the present invention has been made to solve the above-mentioned problems occurring in the prior arts, and it is an object of the present invention to provide a surgical navigation instrument having a temperature sensor which is detachably mounted through screw-coupling of a handpiece and electrodes, thereby easily performing an autoclave action to remove microorganisms using saturated steam with respect to a part which can be contaminated during treatment, and enhancing convenience in replacement of a grip part and the electrodes of the handpiece which are consumables.

To accomplish the above object, according to the present invention, there is provided a surgical navigation instrument having a temperature sensor including: a handpiece housing having an insulator having a contact pin connected with a control unit of a high frequency surgical device by a cable, and an operation button for starting and terminating high frequency output; a handpiece cover unit which covers the handpiece housing and has a first screw thread and a button cover for covering the operation button; an electrode fixing unit having a second screw thread formed on the inner circumferential surface thereof and detachably coupled with the first screw thread to prevent a clearance between the electrode unit and handpiece cover unit during treatment; an electrode unit fixed to the electrode fixing unit and inserted into the human body; and a temperature sensor which is fixed to the handpiece housing, of which one end is connected to the insulator via a harness and the other end penetrates the inside of the electrode unit, and which measures temperature of a surgical site when high frequency is generated from the electrode unit.

Moreover, an operation state display unit is formed at an end of the handpiece housing.

Furthermore, the operation state display unit has a three-color LED light emitting structure composed of a green light showing a high frequency output standby mode, a blue light showing a high frequency output state, and a red light showing a temperature warning and an error occurrence state.

Additionally, an operation state display window is formed at one end of the handpiece cover unit to allow a user to see the operation state display unit.

In addition, a handle grip portion is formed on the outer circumferential surface of the handpiece cover unit.

Moreover, a hook locking part is formed on the inner circumferential surface of at the other end of the handpiece cover unit.

Furthermore, the coupling of the handpiece housing and the handpiece cover unit is guided by a coupling guide unit to prevent mis-insertion due to the coupling and to minimize a clearance by rotation during the treatment.

Additionally, the coupling guide unit includes: at least one first coupling guide formed on the outer circumferential surface of the handpiece housing; and at least one second coupling guide formed on the inner circumferential surface of the handpiece cover unit to correspond to the first coupling guide.

In addition, the first coupling guide has a groove structure or protrusion structure, and the second coupling guide has a protrusion structure or groove structure.

Moreover, the electrode unit includes: an electrode rod having a hollow part through which the temperature sensor passes; an electrode tip formed on the front end of the electrode rod; and a coating layer coated on the outer circumferential surface of the electrode rod.

Furthermore, the temperature sensor has a probe rod which extends to the electrode tip through the hollow part of the electrode rod to measure temperature of the surgical site when high frequency is applied to the electrode tip.

Additionally, the electrode tip is made of a SUS material capable of performing the autoclave action, and the coating layer is a Teflon coated layer capable of performing the autoclave action.

In addition, the handpiece cover unit is made of a silicon material capable of performing the autoclave action.

Furthermore, the electrode fixing unit is made of a polysulfone material capable of performing the autoclave action.

According to the present invention, the surgical navigation instrument having a temperature sensor is detachably mounted through screw-coupling of a handpiece and electrodes, thereby easily performing an autoclave action to remove microorganisms using saturated steam with respect to a part which can be contaminated during treatment, and enhancing convenience in replacement of a grip part and the electrodes of the handpiece which are consumables.

The effects of the present invention are not limited to the above-mentioned effects and further effects not described above will be clearly understood by those skilled in the art.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Hereinafter, embodiments of the present invention will be described in detail with reference to the accompanying drawings.

Figure 1:
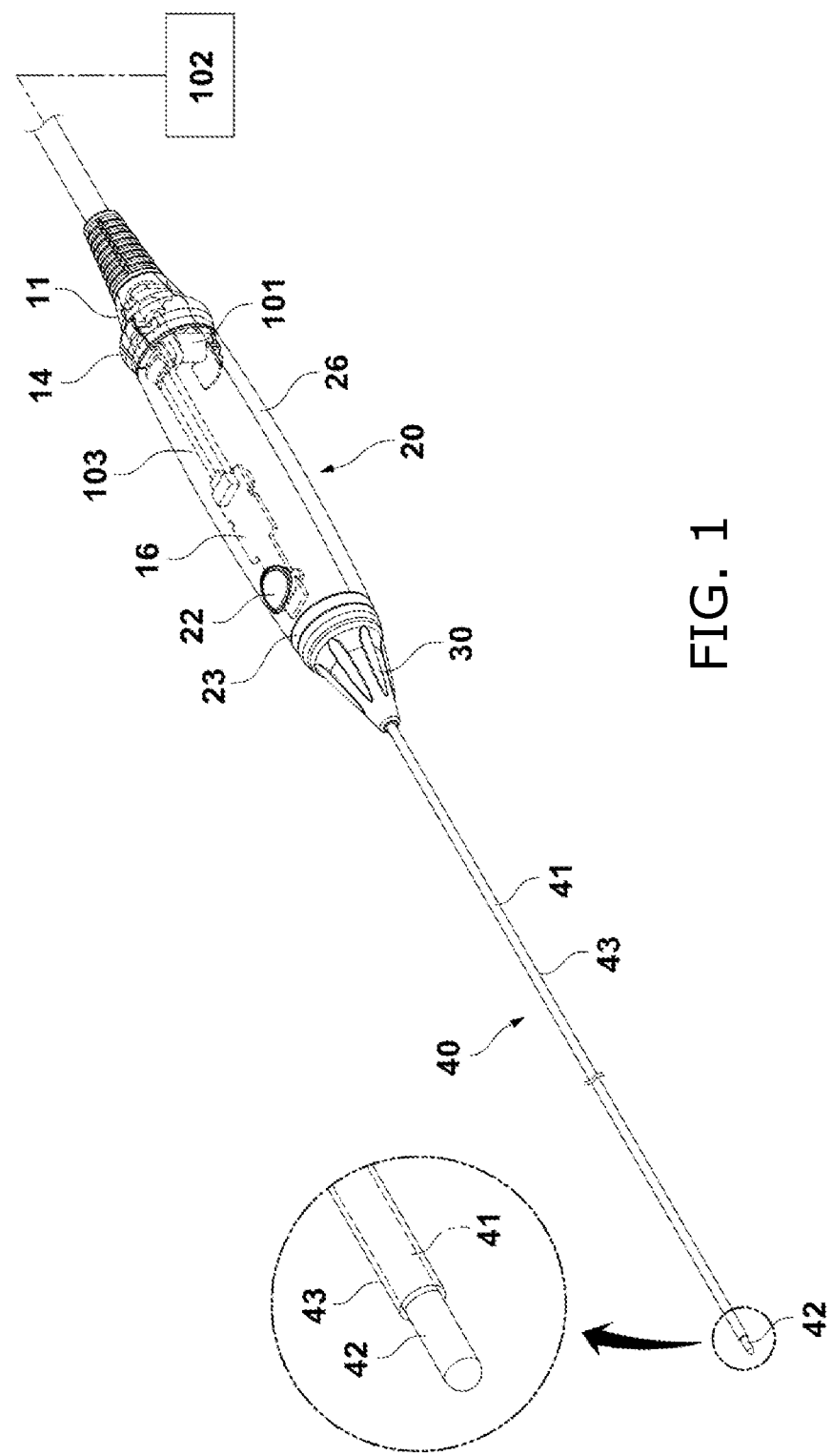
FIG. 1 is a perspective view illustrating a surgical navigation instrument having a temperature sensor according to an embodiment of the present invention.
Figure 2:
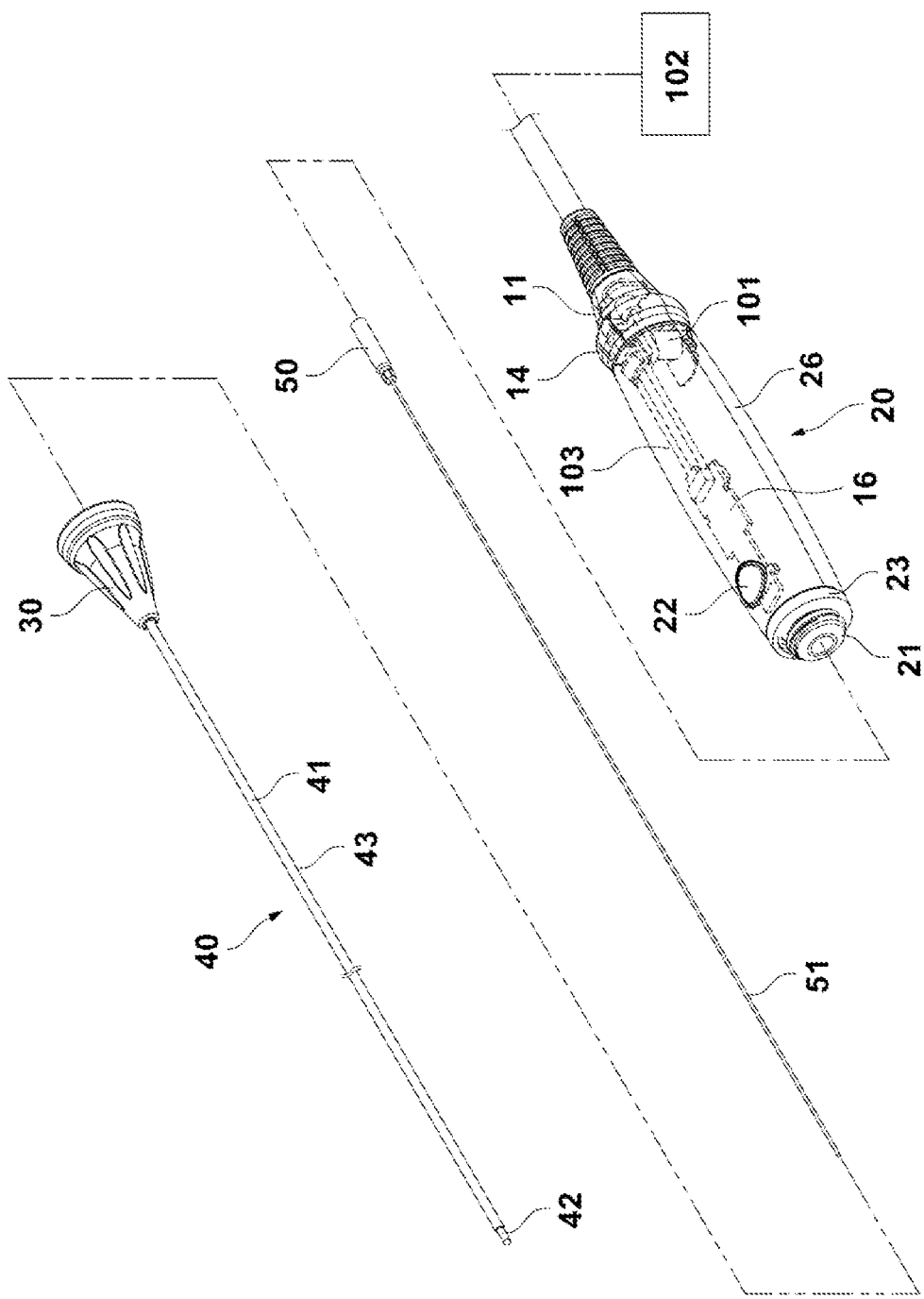
FIG. 2 is an exploded view illustrating a handpiece, an electrode unit, and a temperature sensor according to the embodiment of the present invention.
Figure 3:
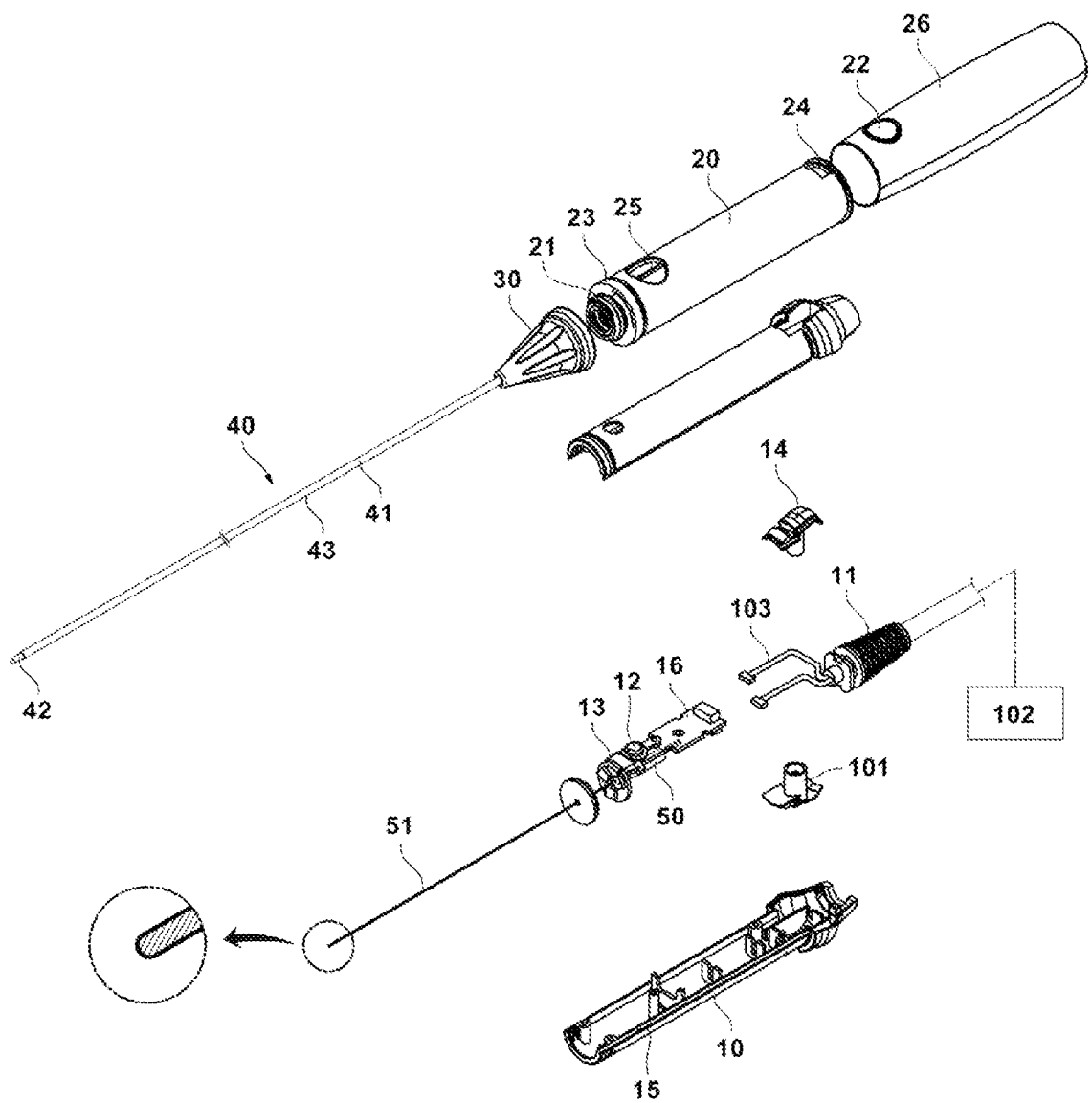
FIG. 3 is an exploded perspective view illustrating the surgical navigation instrument having the temperature sensor according to the embodiment of the present invention.
Figure 4:
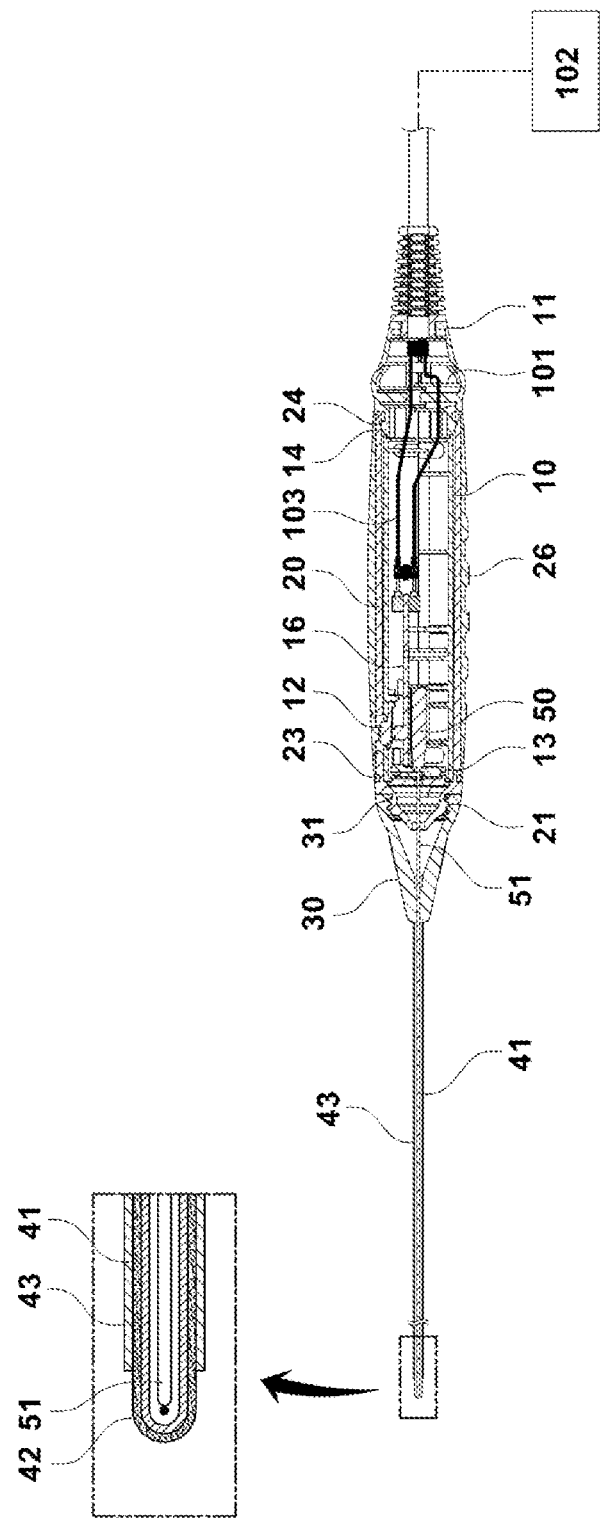
FIG. 4 is an enlarged sectional view illustrating the surgical navigation instrument having the temperature sensor according to the embodiment of the present invention.
Figure 5:
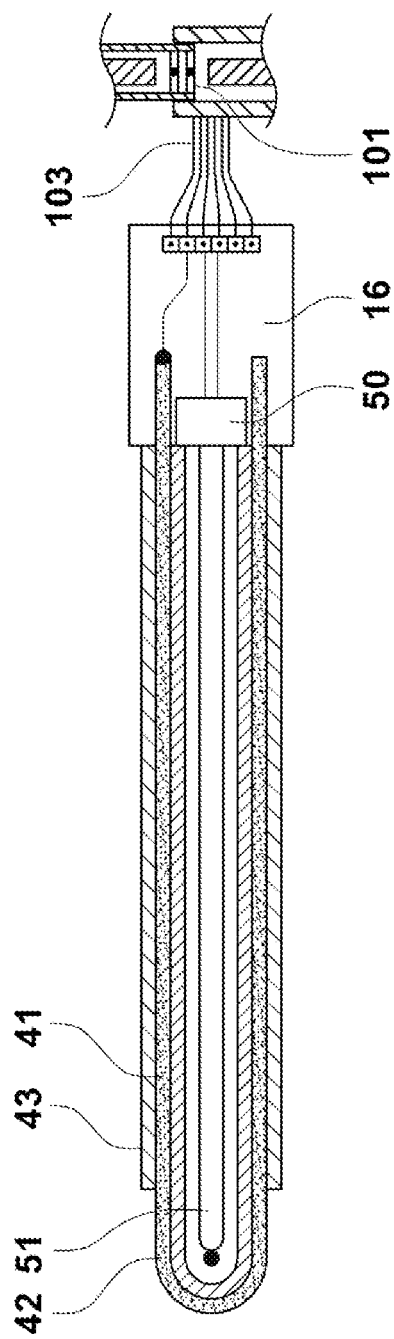
FIG. 5 is a diagram illustrating an electrical connection between the electrode unit, the temperature sensor, the harness, and the contact pin according to the embodiment of the present invention.

FIG. 1 is a perspective view illustrating a surgical navigation instrument having a temperature sensor according to an embodiment of the present invention, FIG. 2 is an exploded view illustrating a handpiece, an electrode unit, and a temperature sensor according to the embodiment of the present invention, FIG. 3 is an exploded perspective view illustrating the surgical navigation instrument having the temperature sensor according to the embodiment of the present invention, and FIG. 4 is an enlarged sectional view illustrating the surgical navigation instrument having the temperature sensor according to the embodiment of the present invention, and FIG. 5 is a diagram illustrating an electrical connection between the electrode unit, the temperature sensor, the harness, and the contact pin according to the embodiment of the present invention.

Referring to FIGS. 1 to 5, the surgical navigation instrument having the temperature sensor according to the embodiment of the present invention includes a handpiece housing 10, a handpiece cover unit 20, an electrode fixing unit 30, an electrode unit 40, and a temperature sensor 50.

The handpiece housing 10 is connected to a control unit 102 of a high frequency surgical device by a cable, and includes an insulator 11 having a contact pin (101), an operation button 12 for starting and terminating high frequency output, an operation state display unit 13, and at least one hook 14.

Here, the operation state display unit 13 may have a three-color LED light emitting structure composed of a green light showing a high frequency output standby mode, a blue light showing a high frequency output state, and a red light showing a temperature warning and an error occurrence state. The operation state display unit 13 is electrically connected to a circuit board 16 accommodated in the handpiece housing 10 together with the operation button 12.

On the other hand, the insulator 11 is coupled to the rear end of the handpiece housing 10 so that the fat fluid sucked through an electrode tip 42 included in the electrode portion 40 flows, and the contact pin 101 is formed on the inner surface of the insulator 11 for interface with the high frequency surgical device. The temperature sensor 50 is connected to the contact pin 101 via a harness 103 so as to be electrically connected with the high frequency surgical device.

Moreover, although not shown in the drawings, the high-frequency surgical device includes: a liposuction device having a liposuction pump; and a fat storage container in which fat sucked through a fat suction pipe is accumulated; and an operation unit allowing a user to manually adjust the suction strength of the liposuction pump, the high frequency output of the high frequency output unit, and the like when necessary.

The handpiece cover unit 20 is made of a silicone material capable of withstanding an autoclave action to cover the handpiece housing 10, and includes: a first screw thread 21 for coupling with the electrode fixing unit 30; a button cover 22 for covering the operation button 12; an operation state display window 23; and one or more hook locking part 24.

The operation state display window 23 is configured to see the operation state display unit 13 formed in the handpiece housing 10 when the handpiece cover unit 20 is coupled to the handpiece housing 10.

The hook locking part 24 is formed at the other end of the handpiece cover unit 20 so that the hook 14 formed on the outer circumferential surface of the other end of the handpiece housing 10 is caught when the handpiece cover unit 20 is coupled to the handpiece housing 10.

Here, a handle grip portion 26 may be formed on the outer circumferential surface of the handpiece cover unit 20 to increase the grip feeling of the user.

On the other hand, the coupling of the handpiece housing 10 and the handpiece cover unit 20 may be guided by a coupling guide unit composed of first and second coupling guides 15 and 25 so as to minimize a clearance caused by rotation during treatment while preventing erroneous insertion due to the coupling of the hand piece housing 10 and the handpiece cover unit 20.

In other words, at least one first coupling guide 15 has a groove structure or protrusion structure formed on the outer circumferential surface of the handpiece housing 10, and the second coupling guide 15 has a groove structure or a protrusion structure formed on the inner circumferential surface of the handpiece cover unit 20.

Therefore, the second coupling guide 25 which is formed on the inner circumferential surface of the handpiece cover unit 20 when the handpiece cover unit 20 is coupled to the outer circumferential surface of the handpiece housing 10 is coupled to the handpiece housing 10 in a way of sliding along the first coupling guide 15 formed on the outer circumferential surface of the handpiece housing 10 so as to cover the handpiece housing 10.

The electrode fixing unit 30 is made of a polysulfone material capable of withstanding the autoclave action, and has a second screw thread 31 formed on the inner circumferential surface thereof. The second screw thread 31 may be fastened to a first screw thread 21 formed in the handpiece housing 10, thereby preventing a clearance between the electrode unit 40 and handpiece cover unit 20 during treatment.

The electrode unit 40 is fixed to the electrode fixing unit 30 and is inserted into the human body, and includes an electrode rod 41, an electrode tip 42, and a coating layer 43.

The electrode rod 41 is made of a SUS material capable of withstanding the autoclave action, has a hollow part (not shown) through which the temperature sensor 50 passes, and is fixed to the electrode fixing part 30.

The electrode tip 42 is made of a SUS material capable of withstanding the autoclave action, and is formed on the front end of the electrode rod 41.

The coating layer 43 is a Teflon coated layer capable of withstanding the autoclave action, and is coated on the outer circumferential surface of the electrode rod 41.

Here, the coating layer 43 is formed only on the outer circumferential surface of the electrode rod 41 so that high frequency output is performed only at the electrode tip 42.

On the other hand, in the descriptions of the hand piece cover unit 20, the electrode fixing unit 30, and the electrode unit 40, they are limited to the materials for the autoclave action, but they are not limited to the materials, and any material which does not cause denaturation even by heat of about 132°, sterilization time of about 20 minutes, and autoclave actions of about ten times to remove microorganisms using saturated vapor.

The temperature sensor 50 is fixed to the handpiece housing 10, and has a probe rod 51 having one end connected to the hand piece housing 10 and the other end passing through the inside of the electrode rod 41 of the electrode unit 40. The temperature sensor 50 measures temperature of the surgical site through the probe rod 51 when high frequency occurs in the electrode unit 40 inserted into the human body.

At this time, the temperature sensor 50 controls the high frequency output of the electrode tip 42 by measuring temperature of the surgical site by occurrence of high frequency so as to prevent the biological tissues from getting scalded by high heat generated by excessive high frequency output, and to uniformly maintain the electrode tip 42 at temperature to optimize fat dissolving of the surgical site. The temperature sensor 50 may be configured in a circular or rectangular shape.

That is, the temperature sensor 50 is extended through the probe rod 51 to the electrode tip 42 to apply high frequency to the electrode tip 42, detects the temperature of the surgical site generated when high frequency is applied, and transmits the temperature. An electric wire for applying high frequency to the electrode tip 42 is connected electrically, so that high frequency of a predetermined level applied through the handpiece is transferred to the electrode tip 42 through the electric wire and temperature of the surgical site can be sensed by the temperature sensor 50 when high frequency is output to the biological tissues from the electrode tip 42.

As illustrated in FIGS. 1 to 5, when an ON signal is output through an operation unit, the high frequency is applied to the electrode tip 42 of the electrode unit 40 via a temperature sensor 50 through a wire.

That is, since the coated layer 43 is formed on the outer circumferential surface of the electrode rod 41 of the electrode portion 40, when high frequency is output to the electrode tip 42 through the temperature sensor 50, the electrode rod 41 does not output high frequency at the handpiece housing 10 and the handpiece cover unit 20, but outputs high frequency output only at the electrode tip 42 inserted into the biological tissues.

After that, when the user holds the handpiece cover unit 20 and inserts the electrode tip 42 into the surgical site of the biological tissues, and then, repeatedly moves it forwards and backwards, fat in the biological tissues is dissolved by the high frequency output from the electrode tip 42.

At this time, the temperature sensor 50 connected to the electrode tip 42 measures temperature of the surgical site of the biological tissues when the high frequency output is made to the electrode tip 42. A control unit (102) of the high frequency surgical device automatically adjusts the high frequency output amount according to the corresponding surgical site through a high frequency output unit (not shown) from the measured temperature so as to minimize tissue damage of the surgical site.

In other words, the temperature of the surgical site measured by the temperature sensor 50 is transmitted to the control unit 102 of the high frequency surgical apparatus through the contact pin 101 of the insulator 11 connected to the temperature sensor 50 via the harness 103. The control unit 102 determines whether the sensed temperature approaches the set temperature or exceeds the set temperature range, and automatically controls the level of the high frequency output or blocks the high frequency according to the determination result.

In other words, if the temperature of the surgical site sensed by the temperature sensor 50 does not reach the set temperature range since a current amount is not reduced according to the sensed impedance change, the control unit 102 continuously controls the high frequency output by the high frequency output unit to dissolve fat in the biological tissues. However, if the temperature of the surgical site sensed by the temperature sensor 50 reaches the set temperature range, the control unit 102 blocks high frequency output for dissolving fat so as to prevent the high frequency output from damaging the tissues of the surgical site or influencing on the tissues around the biological tissues due to the high frequency output which is not controlled properly.

Meanwhile, since contamination may occur during or after treatment, the hook coupling between the handpiece housing 10 and the handpiece cover unit 20 is released, and the handpiece cover unit 20 is separated. Next, the screw coupling between the handpiece cover unit 20 and the electrode fixing unit 30 is released to separate the electrode fixing unit 30 and separate the electrode unit 40 from the electrode fixing unit 30.

Then, the autoclave action is performed to the handpiece cover unit 20, the electrode fixing unit 30, and the electrode unit 40 in order to remove microorganisms using saturated vapor.

In other words, because the handpiece cover unit 20, the electrode fixing unit 30, and the electrode unit 40 are all made of materials capable of withstanding the autoclave action, the handpiece cover unit 20, the electrode fixing unit 30, and the electrode unit 40 can be sterilized and reusable by the autoclave action at heat of about 132° and sterilization time of about 20 minutes using a method of removing microorganisms using saturated vapor. The re-use can be effectively performed till the autoclave action is repeated about ten times.

On the other hand, since the handpiece cover unit 20, the electrode fixing unit 30, and the electrode unit 40 are consumable, the replacement of the hand piece cover unit 20 and the electrode fixing unit 30 and the electrode unit 40 can be selectively and conveniently performed.

In other words, the handpiece cover unit 20 is hook-coupled to the handpiece housing 10, the electrode fixing unit 30 is screw-coupled to the handpiece cover unit 20, and the electrode unit 40 is forcedly fit to the electrode fixing unit 30 so that the electrode unit 40 can be easily separated and replaced.

As described above, while the surgical navigation instrument having the temperature sensor according to the present invention has been described with reference to the attached drawings, it will be understood by those of ordinary skill in the art that the above embodiments of the present invention are all exemplified and are not to limit the technical idea of the present invention.

Therefore, the present invention is not limited to the described embodiments, and it will be understood by those of ordinary skill in the art that various changes, modifications, and equivalents may be made therein without departing from the technical idea and scope of the present invention and such changes, modifications, and equivalents belong to the claims of the present invention.

What is claimed is:

1. A surgical navigation instrument having a temperature sensor comprising:
    a handpiece housing having an insulator having a contact pin connected with a control unit of a high frequency surgical device by a cable, and an operation button for starting and terminating high frequency output;
    a handpiece cover unit which covers the handpiece housing and has a first screw thread and a button cover for covering the operation button;
    an electrode fixing unit having a second screw thread formed on the inner circumferential surface thereof and detachably coupled with the first screw thread to prevent a clearance between the electrode unit and handpiece cover unit during treatment;
    an electrode unit fixed to the electrode fixing unit and configured to be inserted into the human body; and
    a temperature sensor which is fixed to the handpiece housing, of which one end is connected to the insulator via a harness and the other end penetrates the inside of the electrode unit, and which measures temperature of a surgical site when high frequency is generated from the electrode unit,
    wherein the coupling of the handpiece housing and the handpiece cover unit is guided by a coupling guide unit to prevent mis-insertion due to the coupling and to minimize a clearance by rotation during the treatment.

2. The surgical navigation instrument according to claim 1, wherein an operation state display unit is formed at an end of the handpiece housing.

3. The surgical navigation instrument according to claim 2, wherein the operation state display unit has a three-color LED light emitting structure composed of a green light showing a high frequency output standby mode, a blue light showing a high frequency output state, and a red light showing a temperature warning and an error occurrence state.

4. The surgical navigation instrument according to claim 2, wherein an operation state display window is formed at one end of the handpiece cover unit to allow a user to see the operation state display unit.

5. The surgical navigation instrument according to claim 1, wherein a handle grip portion is formed on the outer circumferential surface of the handpiece cover unit.

6. The surgical navigation instrument according to claim 1, wherein a hook locking part is formed on an inner circumferential surface of an end of the handpiece cover unit.

7. The surgical navigation instrument according to claim 1, wherein the coupling guide unit comprises:
    at least one first coupling guide formed on the outer circumferential surface of the handpiece housing; and
    at least one second coupling guide formed on the inner circumferential surface of the handpiece cover unit to correspond to the first coupling guide.

8. The surgical navigation instrument according to claim 7, wherein the first coupling guide has a groove structure or protrusion structure, and the second coupling guide has a protrusion structure or groove structure.

9. The surgical navigation instrument according to claim 1, wherein the electrode unit comprises:
    an electrode rod having a hollow part through which the temperature sensor passes;
    an electrode tip formed on the front end of the electrode rod; and
    a coating layer coated on the outer circumferential surface of the electrode rod.

10. The surgical navigation instrument according to claim 9, wherein the temperature sensor has a probe rod which extends to the electrode tip through the hollow part of the electrode rod to measure temperature of the surgical site when high frequency is applied to the electrode tip.

11. The surgical navigation instrument according to claim 9, wherein the electrode tip is made of a SUS material capable of withstanding an autoclave action, and
    wherein the coating layer is a Teflon coated layer capable of withstanding the autoclave action.

12. The surgical navigation instrument according to claim 1, wherein the handpiece cover unit is made of a silicon material capable of withstanding an autoclave action.

13. The surgical navigation instrument according to claim 1, wherein the electrode fixing unit is made of a polysulfone material capable of withstanding an autoclave action.

* * * * *